(12) United States Patent
Hott et al.

(10) Patent No.: US 12,336,840 B2
(45) Date of Patent: Jun. 24, 2025

(54) VOICE-BASED MONITORING AND ALERTING FOR REMOTE DECOMPENSATED HEART FAILURE DETECTION

(71) Applicant: Noah Labs UG (haftungsbeschraenkt), Berlin (DE)

(72) Inventors: Marcus Hott, Berlin (DE); Oliver Piepenstock, Berlin (DE)

(73) Assignee: Noah Labs GmbH, Berlin (DE)

( * ) Notice: Subject to any disclaimer, the term of this patent is extended or adjusted under 35 U.S.C. 154(b) by 0 days.

(21) Appl. No.: 18/520,875

(22) Filed: Nov. 28, 2023

(65) Prior Publication Data

US 2025/0000445 A1 Jan. 2, 2025

Related U.S. Application Data

(60) Provisional application No. 63/524,375, filed on Jun. 30, 2023.

(51) Int. Cl.
| | | |
|---|---|---|
| *A61B 5/02* | (2006.01) | |
| *A61B 5/00* | (2006.01) | |
| *A61B 7/00* | (2006.01) | |
| *G16H 50/20* | (2018.01) | |
| *G10L 15/02* | (2006.01) | |
| *G10L 25/51* | (2013.01) | |

(52) U.S. Cl.
CPC ............ *A61B 5/4803* (2013.01); *A61B 5/02* (2013.01); *A61B 5/6898* (2013.01); *A61B 5/7267* (2013.01); *A61B 5/7275* (2013.01); *A61B 5/746* (2013.01); *A61B 7/00* (2013.01); *G16H 50/20* (2018.01); *G10L 15/02* (2013.01); *G10L 25/51* (2013.01)

(58) Field of Classification Search
CPC ....... A61B 5/4803; A61B 5/02; A61B 5/6898; A61B 5/7267; A61B 5/7275; A61B 5/746; G16H 50/20
See application file for complete search history.

(56) References Cited

U.S. PATENT DOCUMENTS

| | | | |
|---|---|---|---|
| 10,643,639 B2 * | 5/2020 | Zadgaonkar | A61B 5/4803 |
| 10,796,805 B2 | 10/2020 | Lotan et al. | |
| 10,847,177 B2 | 11/2020 | Shallom | |
| 11,011,188 B2 | 5/2021 | Shallom | |
| 11,024,327 B2 | 6/2021 | Shallom | |
| 11,417,342 B2 | 8/2022 | Shallom | |
| 11,484,211 B2 | 11/2022 | Shallom | |
| 11,538,490 B2 | 12/2022 | Shallom | |
| 11,610,600 B2 | 3/2023 | Shallom | |
| 11,727,954 B2 | 8/2023 | Lotan et al. | |

(Continued)

OTHER PUBLICATIONS

Amir, O et al., "Remote Speech Analysis in the Evaluation of Hospitalized Patients with Acute Decompensated Heart Failure", JACC: Heart Failure, vol. 10, No. 1, 2022, 9 pages. (Year: 2022).*

(Continued)

*Primary Examiner* — Eric F Winakur
(74) *Attorney, Agent, or Firm* — Nixon & Vanderhye P.C.

(57) ABSTRACT

A machine learning based patient voice monitoring and analysis system can reduce the need for patient hospitalization by early detection and treatment of health conditions such as acute decompensated heart failure.

9 Claims, 6 Drawing Sheets

(56) References Cited

U.S. PATENT DOCUMENTS

| | | | |
|---|---|---|---|
| 2012/0220899 A1* | 8/2012 | Oh | A61B 5/4803 600/586 |
| 2012/0265024 A1* | 10/2012 | Shrivastav | A61B 5/4803 600/300 |
| 2018/0203978 A1* | 7/2018 | Basu | G16H 50/20 |
| 2019/0080803 A1 | 3/2019 | Lotan et al. | |
| 2019/0362740 A1* | 11/2019 | Hauptman | A61B 5/4803 |
| 2020/0077940 A1* | 3/2020 | Srivastava | A61B 5/7275 |
| 2022/0165295 A1 | 5/2022 | Shallom | |
| 2023/0306985 A1 | 9/2023 | Haimi-Cohen et al. | |
| 2023/0317099 A1 | 10/2023 | Haimi-Cohen et al. | |

OTHER PUBLICATIONS

Maor, E et al., "Vocal Biomarker Is Associated With Hospitalization and Mortality Among Heart Failure Patients", Journal of the American Heart Association, vol. 9, Issue 7, Apr. 9, 2020, 15 pages. (Year: 2020).*

Wu, F et al., "Trends in voice characteristics in patients with heart failure (VENTURE) in Switzerland: Protocol for a longitudinal observational pilot study", PLOS One, Apr. 5, 2023, pp. 1-13. (Year: 2023).*

Amir et al, "A Novel Approach Using Remote Speech Analysis in Chronic Ambulatory Heart Failure Patients Allows Early Detection of Clinical Decompensation Leading to Hospitalization", Journal of Cardiac Failure, vol. 26, Issue 10, Supplement, p. S89, https://doi.org/10.1016/j.cardfail.2020.09.261, Oct. 2020.

https://web.archive.org/web/20230530195502/https://www.cordiomed.com/ (Jun. 2023).

"Congestive Heart Failure", Cleveland Clinic, last reviewed by a Cleveland Clinic medical professional on Mar. 10, 2023, https://my.clevelandclinic.org/health/diseases/17069-heart-failure-understanding-heart-failure.

Allen et al., "Management of acute decompensated heart failure", CMAJ 176(6):797-805, doi: 10.1503/cmaj.051620, Mar. 13, 2007.

Kerexeta et al, "Prediction and Analysis of Heart Failure Decompensation Events Based on Telemonitored Data and Artificial Intelligence Methods", J Cardiovasc Dev Dis. Feb. 2023; 10(2): 48, doi: 10.3390/jcdd10020048, published online Jan. 28, 2023.

Murton et al, "Acoustic speech analysis of patients with decompensated heart failure: A pilot study", J Acoust Soc Am 142, EL401-EL407, https://doi.org/10.1121/1.5007092, published online Oct. 24, 2017.

ClinicalTrials.gov Identifier: NCT02555904 (Semigran study).

* cited by examiner

VOICE-BASED MONITORING AND ALERTING FOR REMOTE DECOMPENSATED HEART FAILURE DETECTION

CROSS-REFERENCES TO RELATED APPLICATIONS

Priority is claimed from U.S. Provisional Patent Application No. 63/524,375 filed Jun. 30, 2023, incorporated herein by reference for all purposes.

STATEMENT REGARDING FEDERALLY SPONSORED RESEARCH OR DEVELOPMENT

None.

FIELD

The technology herein relates to medical diagnostic techniques and devices, and more particularly to techniques and devices that diagnose medical condition based on speech patterns. Still more particularly, the technology herein relates to techniques and devices that receive audio representing a subject's phonation and in response is able to diagnose acute decompensated heart failure.

BACKGROUND

Congestive heart failure (HF) is a long-term condition in which your heart can't pump blood well enough to meet your body's needs. Your heart is still working. But because it can't handle the amount of blood it should, blood builds up in other parts of your body. Most of the time, it collects in your lungs, legs and feet. See https://my.clevelandclinic.org/health/diseases/17069-heart-failure-understanding-heart-failure There are four heart failure stages (Stages A, B, C and D). They range from having a high risk of developing heart failure to having advanced heart failure. Stage A (pre-heart failure) means you're at a high risk of developing heart failure because you have a family history of congestive heart failure or you have one or more certain medical conditions such as hypertension, diabetes, coronary artery disease, etc. Stage B (pre-heart failure) means your left ventricle isn't working well and/or is structurally abnormal but you've never had symptoms of heart failure. People with Stage C heart failure have a congestive heart failure diagnosis and currently have or previously had signs and symptoms of the condition. People who have Stage D HFrEF (heart failure with reduced ejection fraction) have advanced symptoms that don't get better with treatment. This is the final stage of heart failure. Id.

HF is not "all or nothing"—it can be treated in a variety of ways. However, it can also lead to medical emergencies. Chronic stable HF may easily "decompensate" due to intercurrent illness such as pneumonia, myocardial infarction (a heart attack), abnormal heart rhythms (such as atrial fibrillation), uncontrolled high blood pressure, or the patient's failure to maintain a fluid restriction, diet, or medication. Acute decompensated heart failure (ADHF) is a clinical syndrome of worsening signs or symptoms of heart failure (HF) requiring hospitalization or other unscheduled medical care. Such acute decompensated heart failure (ADHF) can show signs and symptoms of difficulty breathing with physical activity (exertional dyspnea), difficulty breathing while lying flat (orthopnea), episodes of waking up from sleep gasping for air (paroxysmal nocturnal dyspnea), and acute pulmonary edema. See Allen et al, "Management of acute decompensated heart failure", CMAJ 176(6):797-805 (Mar. 13, 2007) doi: 10.1503/cmaj.051620.

The injured heart muscle of a patient with heart failure does not pump blood as efficiently as it should but can nevertheless continue to maintain necessary blood circulation. However, if an additional condition(s) such as a myocardial infarction, a pulmonary infection, anemia thyrotoxicosis, uncontrolled hypertension, excessive salt intake or medication non-compliance occurs, the heart's pumping ability will further decrease and the body's own mechanisms will try to compensate. One way the patient's body tries to compensate is by stimulating the kidneys to produce angiotensin—a hormone that helps regulate blood pressure by constricting or narrowing blood vessels and triggering water and salt (sodium) intake. This mechanism ordinarily will increase blood pressure by making the blood vessels through which the blood flows smaller in diameter. The body also generates aldosterone—a steroid hormone made by the adrenal cortex (the outer layer of the adrenal gland) that helps control the balance of water and salts in the kidney by keeping sodium in and releasing potassium from the body. This mechanism (which helps the body compensate for dehydration) causes the body to retain fluids-giving the heart more fluid to pump.

Unfortunately, in a patient with HF, the angiotensin will construct the arteries that are supplying blood to the heart, making it more difficult for the heart to pump. And the release of aldosterone will cause the renal retention of fluid-but now, there is already more fluid than the heart can pump. In acute decompensated HF, the retained extra fluid will start to cause cardiogenic pulmonary edema, i.e., fluid buildup in the lungs. Dyspnea (difficult or labored breathing) often occurs—caused by rapid accumulation of fluid within the interstitial and alveolar spaces within the lungs-resulting in elevated cardiac filling pressures. The patient may begin to exhibit cough, crackles, wheezing, blood tinged sputum, and tachypnea (abnormally rapid breathing) due to pulmonary congestion because the left side of the heart is unable to pump out blood that is pooling in the lungs.

Thus, the body's compensation mechanisms for the injured heart (vasoconstriction and fluid retention) end up working against the injured heart by making it harder for the heart to pump, creating a steadily worsening condition and eventually a medical emergency. Treatment for such decompensated heart failure may involve diuretics (to get rid of the extra retained fluid), venous and arterial vasodilation (to open up the constricted blood vessels), oxygen and the patient assuming a sitting position (to reduce blood pooling in the lungs).

Much work has been done in the past to monitor patients with HF in order to reduce the chance their condition will spiral into acute decompensated HF. Such monitoring can help ensure the patient takes necessary medications and may in some cases test for weight gain that may indicate edema. Some in the past have trained computational models to try to predict onset based on monitoring patient vital signs and answers to a questionnaire. See e.g., Kerexeta et al, Prediction and Analysis of Heart Failure Decompensation Events Based on Telemonitored Data and Artificial Intelligence Methods, J Cardiovasc Dev Dis. 2023 February; 10(2): 48. Published online 2023 Jan. 28. doi: 10.3390/jcdd10020048.

Meanwhile, it has been recognized that since the amount of pulmonary edema required to measurably change the voice is small, voice monitoring may allow detection and tracking HF-related pulmonary edema at an earlier stage than other techniques such as measuring the body's weight. See Murton et al, "Acoustic speech analysis of patients with decompensated heart failure: A pilot study", J Acoust Soc Am 142, EL401-EL407 (2017) https://doi.org/10.1121/1.5007092; see also ClinicalTrials.gov Identifier: NCT02555904 (Semigran study). These pilot studies had a goal of tracking voice characteristics (e.g., creak or "vocal fry") of patients admitted to a hospital for acute decompensated HF as they received treatment, edema decreased and their bodies retained less water.

It would be desirable to monitor and/or track stable HF patients who are at risk of decompensated HF before they have to enter the hospital, so their health conditions can be treated appropriately before they become emergencies.

DETAILED DESCRIPTION OF EXAMPLE NON-LIMITING EMBODIMENTS

Figure 1:
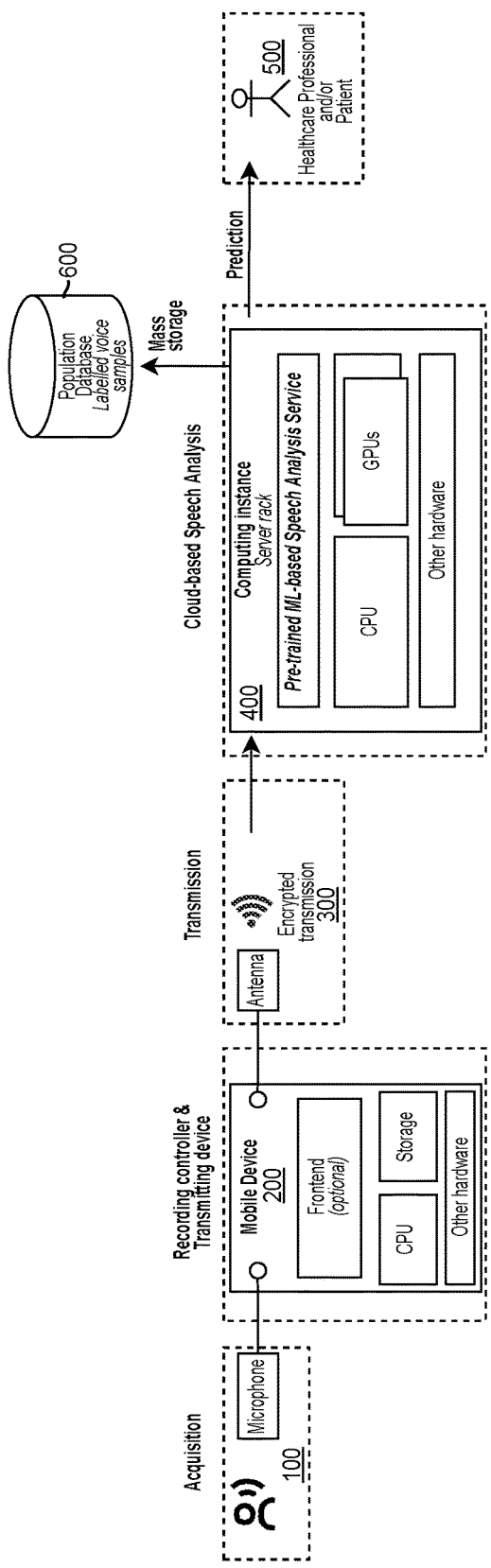
FIG. 1 is an example system block diagram.

FIG. 1 is an example block diagram of an example voice monitoring system. In this example, a microphone is used to detect the voice characteristics of a patient (100). The patient may be asked for example to read a particular script into a microphone. The microphone may be on a smart device such as a smart phone. As noted below, the voice monitoring system may be local to or remote from the patient.

The recording controlling and transmitting device 200 (which may be the smart phone, tablet or other mobile device) may include a front end, a CPU, storage and other hardware including a wireless transmission interface. The mobile device 200 may store and encrypt the sampled, digitized speech of the patient for transmission (300) to a computing instance 400 such as a server for cloud-based speech analysis.

The computing instance 400 may include a CPU, one or more GPUs, and other hardware, capable of efficiently executing a machine learning algorithm such as a deep neural network (DNN). The computing instance 400 stores instructions and is otherwise configured to provide a pretrained machine learning based speech analysis service. It may access a population database 600 providing labelled voice samples for training the machine-learning model. The computing instance 400 generates and provides a prediction to the patient and/or physician 500.

Figure 2:
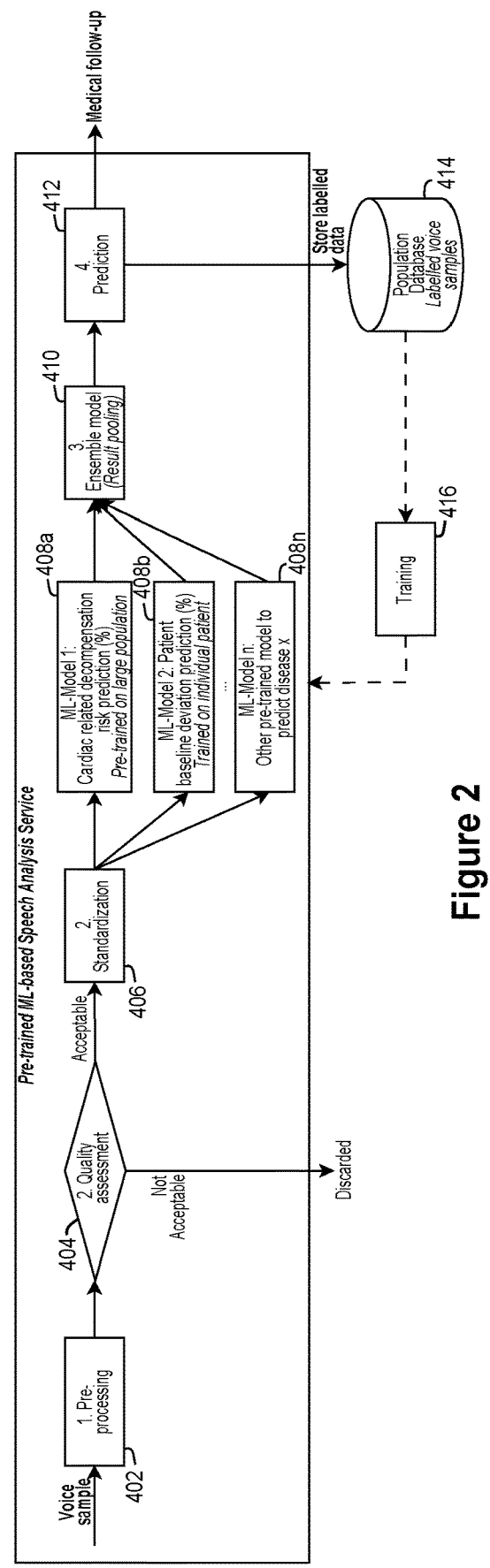
FIG. 2 is an example more detailed process flow including machine learning analysis.

FIG. 2 shows an example process the computing instance 400 performs. After receiving and decrypting a digitized voice sample, the computing instance 400 preprocesses it (402) and tests it for quality (404). The computing instance 400 discards the voice sample if the quality is unacceptable, and otherwise passes it along to the pretrained machine learning based speech analysis service. The pretrained machine learning based speech analysis service normalizes the digital voice sample (406) and then applies it to one or more pretrained machine learning (ML) models for analysis and prediction. The prediction in this case is a prediction that a serious health condition may develop. For example, early pulmonary edema may introduce often subtle features in the patient's speech or voice characteristics (e.g., vocal fry, shallower breathing, creaky voice, increased fundamental frequency, decreased cepstral peak prominence variation, etc.) that may be difficult for a human listener to detect but that may be readily detectable by the ML model as an early sign that the patient is headed for acute decompensated heart failure.

There can be different, alternative ML models:

In one embodiment, a first ML model 408a develops a cardiac related decompensation risk prediction and has been pretrained on a large population. In one example, model 408a is a deep learning model and takes the voice recording as input. It is using a deep layer structure from the encoder-decoder architecture. At the so-called bottleneck, the core information of the input representation is captured in the so-called "embedding". The model is pre-trained on large data in a speech reconstruction task, where the core of bottleneck embeds the voice profile of the speaker. For the purpose of predicting decompensation (cardiac congestion), the decoder part is removed, and custom hidden layers are added. The model is then trained on voice recordings from heart failure patients performed at stable and decompensated conditions. Decompensated conditions were identified as such through knowledge of:
- hospital admissions due to acute decompensated heart failure events
- N-terminal pro b-type natriuretic peptide levels (NT-proBNP)
- intracardiac pressure readings acquired by a catheter or dedicated implant (CardioMEMS)

The model is trained on predicting impending decompensation and does not require a patient-specific baseline recording.

Note: A reference recording can nevertheless be used in practice to reduce the change of false-positive alerts. This may be achieved by comparing the output of the model on a voice recording causing a potential alert, with the output of the model on the baseline recording to ensure a minimum distance, which can be set as a threshold and fine-tuned.

In one embodiment, a second ML model 408b develops a patient baseline deviation prediction based on a model trained on voice samples from that particular patient. This model is thus looking for changes in the voice characteristic(s) of the particular patient that are predictive of an impending decompensated heart failure condition. Model 408b in one particular example uses a patient individual baseline voice recording at stable conditions. The algorithm is composed of three main steps:
1. Step: A feature extraction step where acoustic features, spectral- and cepstral components of the voice recordings are extracted. This step produces a representation of the vocal biomechanics of the speaker.
2. Step: a machine-learning model that combines these features in a learned high-dimensional representation
3. Step: A distance function that considers the latest submitted voice-recording and a reference voice recording.

Note: the reference voice recording may be updated regularly to reflect confirmed stable conditions closer to the present recording.

A further model 408n may develop a prediction for another disease based on speech analysis.

The first ML model 408a and the second ML model 408b can be used alternatively or they may be used together to develop a blending prediction; or the results of one model may be used to confirm the prediction of the other model. See block 410 (ensemble model, result pooling).

Figure 3:
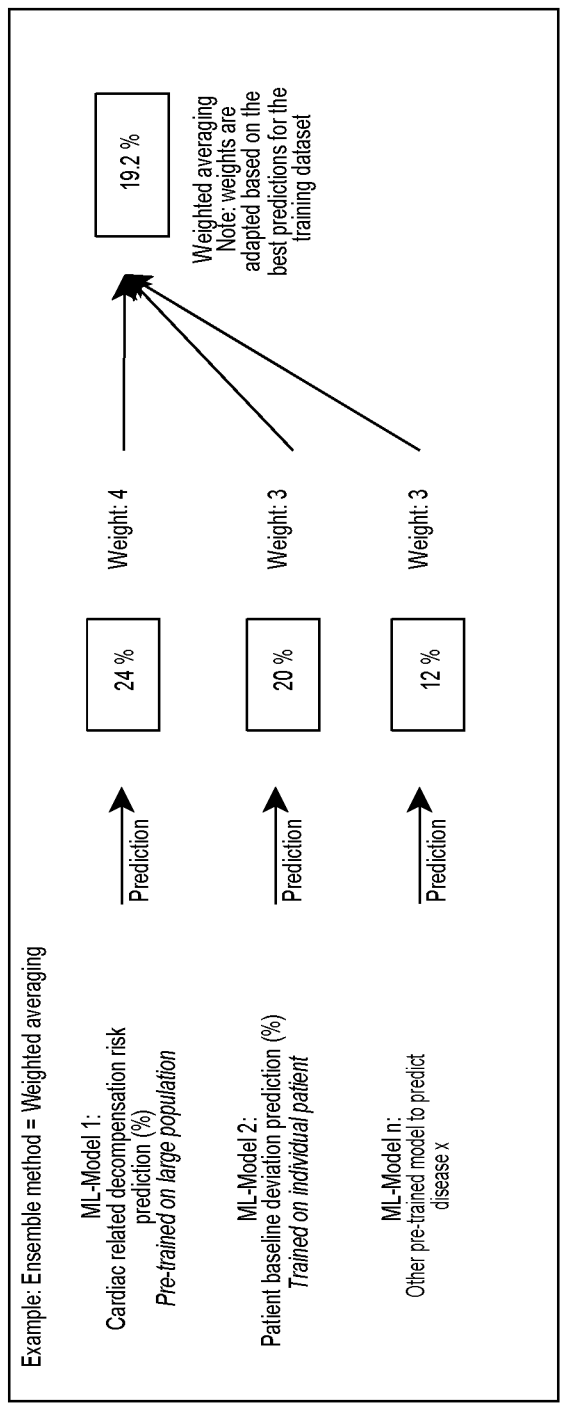
FIG. 3 shows example pooled result processing.

FIG. 3 shows a result pooling example where results of the two ML models described above and result(s) of one or more additional (optional in some embodiments) ML models (e.g., other pre-trained model(s) to predict certain diseases x) are combined using weighted averaging with weights that are adapted based on best predictions for the training dataset(s). In this particular illustrative example, the prediction results of ML Model 1, ML Model 2, and ML Model N are weighted with a ratio of 4:3:3 respectively, to provide a combined or pooled result that is contributed to by each of the ML Model results but that is not determined exclusively by any of the ML Model results but rather represents a combination of each of the ML Model results. Other embodiments could use other methods of combining or pooling results of multiple models such as majority voting, plurality voting, simple averaging, etc.

Another embodiment uses techniques where the user baseline comparison or other data processing is performed without training/machine learning. Such non-ML techniques can for example compare more than one (acoustic) datapoint/feature between the current and baseline recording, thus discerning the impact of multiple acoustic features. At that point using machine learning voice analysis algorithms may generally yield the best results for most patients/use cases, but require available data. However, additional tests or analysis that may or may not be based on voice analysis (e.g., patient medical history) may be used in combination with ML based or other speech analysis.

The resulting prediction (block 412) may be provided to the patient and/or health care provider for medical followup. It may also be stored in a population database 414 as a labelled voice sample and used to further train (416) one or more of the ML models.

Figure 4:
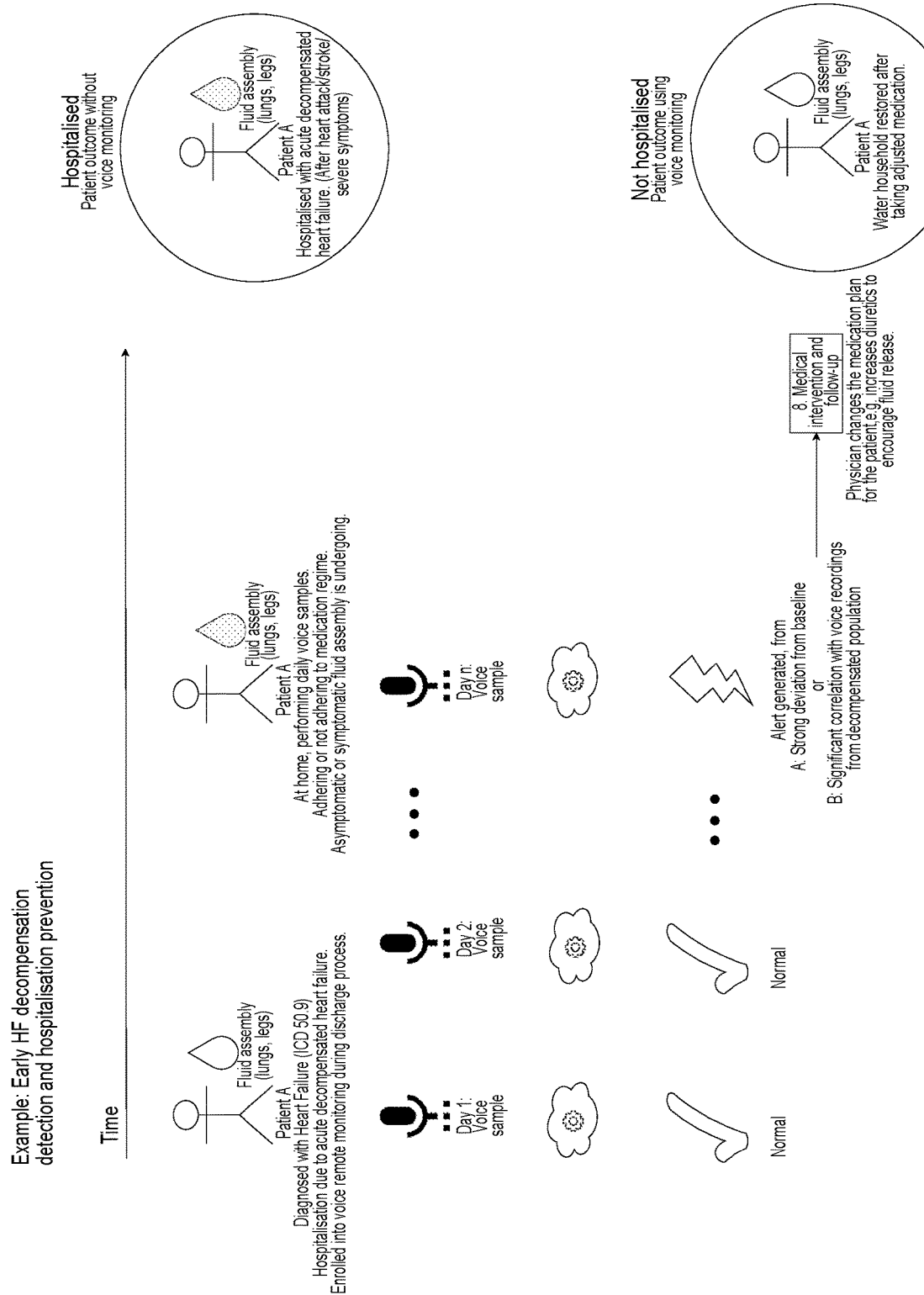
FIG. 4 is an example detailed process flow.

FIG. 4 shows an overall example early HF decompensation detection and hospitalization prevention technique using the system described above. FIG. 4 depicts a patient ("Patient A") who has been diagnosed with heart failure (HF) who was hospitalized due to decompensated HR. After treatment and upon discharge, the patient is enrolled into a voice remote monitoring program.

At home, the patient performs daily voice samplers. Also monitored are adherence or non-adherence to medication regime. Asymptomatic or symptomatic fluid assembly is undergoing. During this time, the daily voice samples are analyzed and determined whether the results are normal (no indication of acute decompensated HR) or abnormal (indication of acute decompensated HR). The Figure shows on day n that an alert is generated based on strong deviation from baseline and/or significant correlation with voice recordings from decompensated population—thus indicating that the patient may have begun suffering from another bout of decompensated HR. At this point, one approach (see upper righthand corner of the Figure) is for the patient to be told to report to the hospital and have the patient examined and hospitalized with acute decompensated HR (e.g., after a heart attack, stroke, or severe symptoms). This is the most likely outcome for a patient who was not using the voice monitoring technology.

However, another approach made possible by the at-home voice sampling/monitoring is for a physician to intervene once the decompensated HR has been detected and before it has become acute. The physician may for example change the medication plan for the patient to prescribe a diuretic that encourages fluid release. Further voice monitoring can be used to confirm that the edema that had begun is now relieved. The patient's outcome is thus no hospitalization in this example-instead the patient's water household is restored without the need for hospitalization. On the other hand, if the changes to medication do not promptly relieve the edema, the patient may be told to report to a cardiologist or to the hospital.

Figure 5:
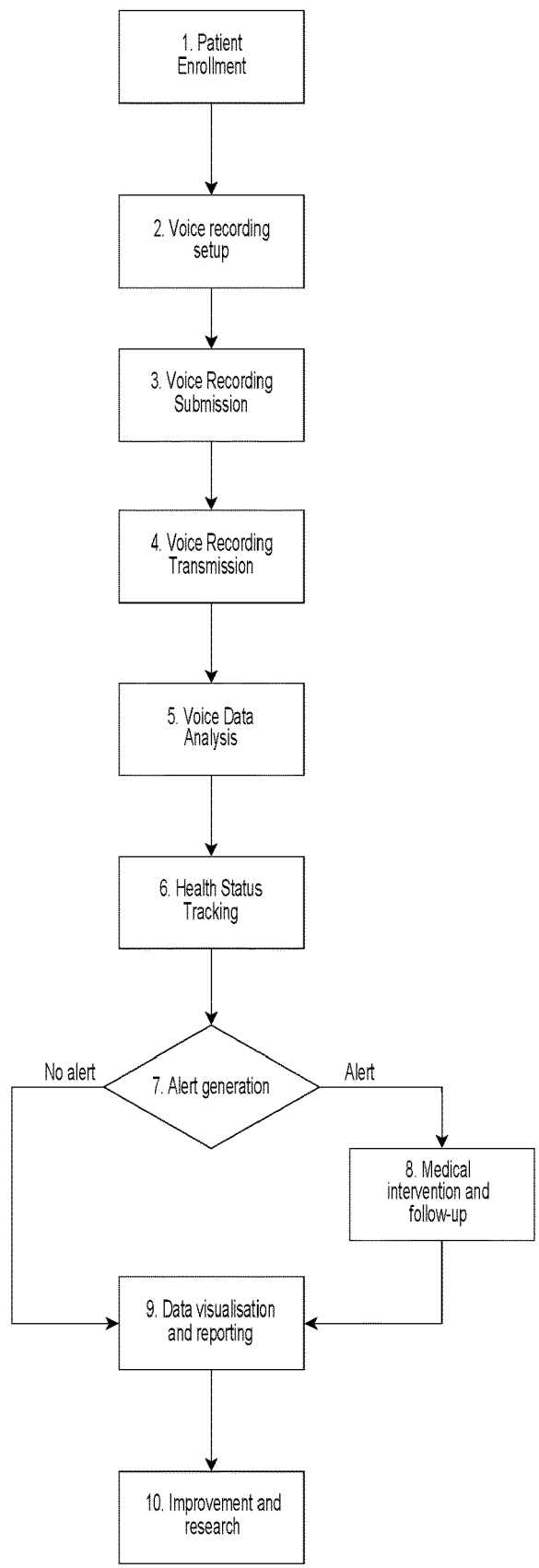
FIG. 5 is an overall schematic flowchart of an example early HF decompensation detection and hospitalization preventing technique.
Figure 5A:
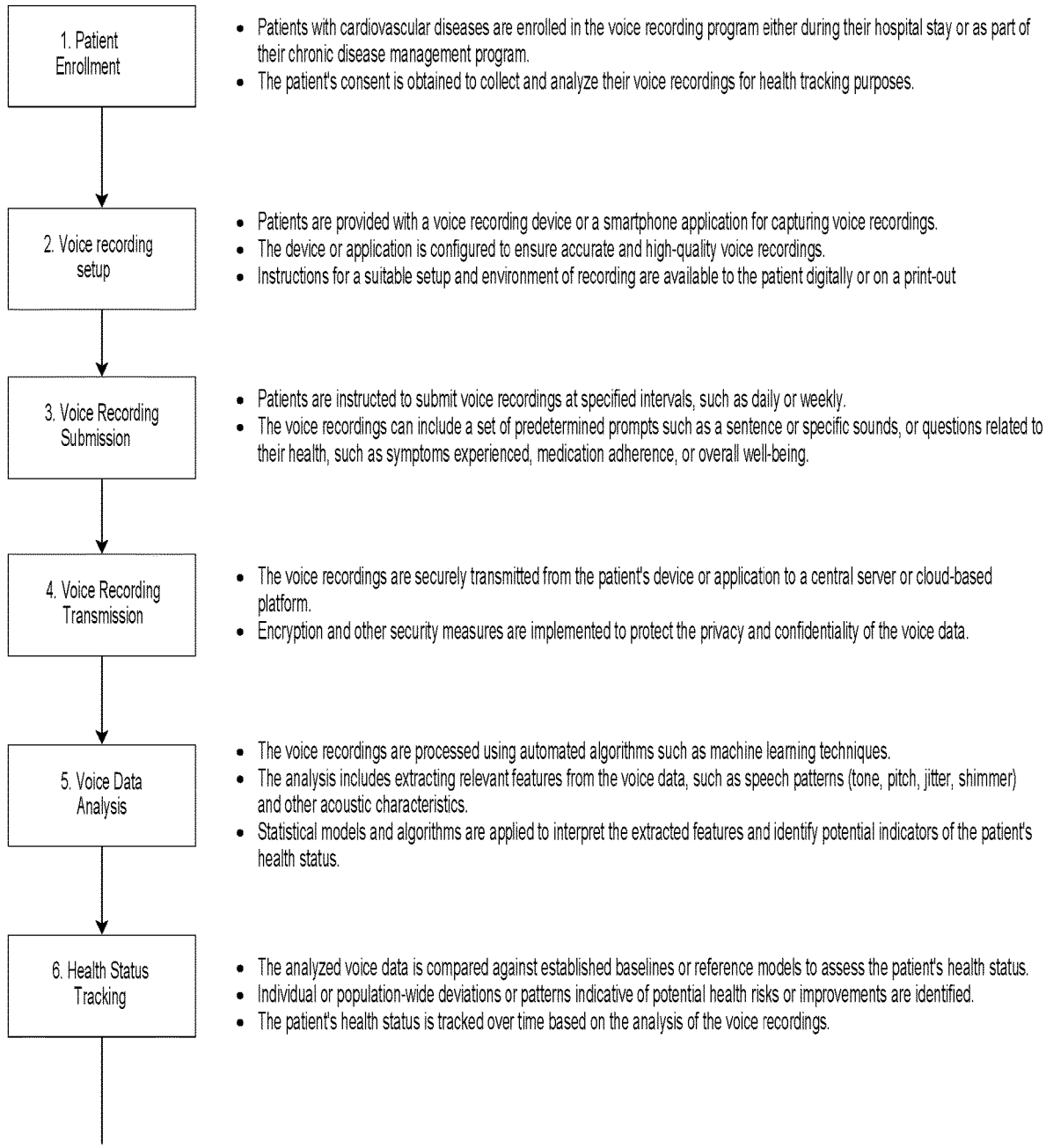
FIGS. 5A & 5B together are an overall process flow.
Figure 5B:
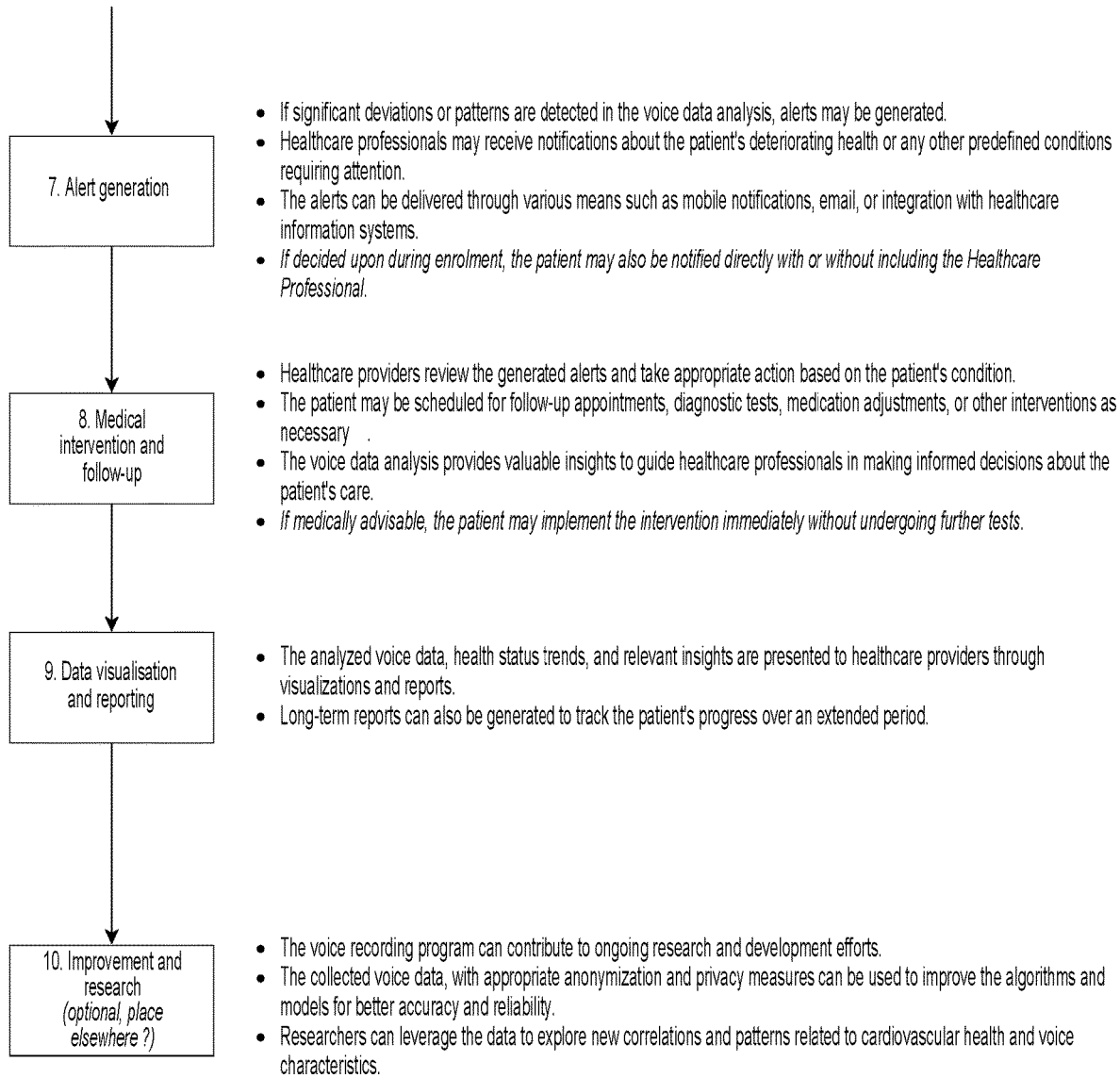

FIG. 5 shows an overall example voice monitoring process flow, including the following steps:
Patient enrollment
Voice recording setup
Voice recording submission
Voice recording transmission
Voice data analysis
Health status tracking
Alert generation (if an alert is generated, then medical intervention and follow is triggered)
Data visualization and reporting
Improvement and research FIG. 5A, 5B shows the FIG. 5 flow with more detailed description of each step as performed by the FIG. 1 system:

Patient Enrollment: Patients with cardiovascular diseases are enrolled in the voice recording program either during their hospital stay or as part of their chronic disease management program. The patient's consent is obtained to collect and analyze their voice recordings for health tracking purposes.

Voice Recording Setup: Patients are provided with a voice recording device or a smartphone application for capturing voice recordings. The device or application is configured to ensure accurate and high-quality voice recording. Instructions for a suitable step and environment of recording are available to the patient digitally or on a printout.

Voice Recording Submission: Patients are instructed to submit voice recordings at specific intervals, such as daily or weekly. The voice recordings can include a set of predetermined prompts such as a sentence or specific sounds, or questions related to their health, such as symptoms experienced, medication adherence, and overall well-being.

Voice Recording Transmission: The voice recordings are securely transmitted from the patient's device or application to a central server or cloud-based platform. Encryption and other security measures are implemented to protect the privacy and confidentiality of the voice data.

Voice Data Analysis: the voice recordings are processed using automated algorithms such as machine learning techniques. The analysis includes extracting relevant features from the voice data, such as speech patterns (tone, pitch, jitter, shimmer) and other acoustic characteristics. Statistical models and algorithms are applied to interpret the extracted features and identify potential indicators of the patient's health status.

Health Tracking Status: the analyzed voice data is compared against established baselines or reference models to assess the patient's health status. Individual and/or population-wide deviation or patterns indicative of potential health risks or improvements are identified. The patient's health status is tracked over time based on the analysis of the voice recordings.

Alert Generation: If significant deviations are detected to the voice data analysis, alerts may be generated. Healthcare professionals may receive notifications about the patient's deteriorating health or other predefined conditions requiring attention. The alerts can be delivered through various means such as mobile notifications, email, or integration with healthcare information systems. If decided during enrollment, the patient may also be notified with or without including the healthcare professional.

Medical Intervention and Followup: healthcare providers review the generated alerts and take appropriate action based on the patient's condition. The patient may be scheduled for follow-up appointments, diagnostic tests, medication adjustments, or other interventions as necessary. The voice data analysis provides valuable insights to guide healthcare professionals in making informed decisions about the patient's care. If medically advisable, the patient may implement the intervention immediately without undergoing further tests.

Data Visualization and reporting: the analyzed voice data, health status trends, and relevant insights are presented to healthcare providers through visualization and reports. Long-term reports can be generated to track the patient's progress over an extended period.

Improvement and Research: The voice recording program can contribute to ongoing research and development efforts. The collected voice data with appropriate anonymization and privacy measures, can be used to improve the algorithms and models for better accuracy and reliability. Researchers can leverage the data to explore new correlations and patterns related to cardiovascular health and voice characteristics.

All patents and publications cited herein are incorporated herein by reference for all purposes.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A detecting and alerting system for detecting onset of decompensated heart failure in remotely-located human subjects and automatically generating an electronic alert based on a detected onset of decompensated heart failure in a remotely-located human subject, the detecting and alerting system comprising:
   a data receiver that receives digitized voice samples of remotely-located human subjects;
   a computing instance operatively connected to the data receiver, the computing instance configured to perform operations comprising:
   (i) executing a first machine learning model trained on voice samples from a population to detect at least one feature in speech or voice characteristics that is a sign of onset of decompensated heart failure,
   (ii) executing a second machine learning model that analyzes changes in acoustic features of voice samples received from the remotely-located human subject over time,
   (iii) blending a first output from the first machine learning model based on voice samples received from the remotely-located human subject with a second output from the second machine learning model based on the voice samples received from the remotely-located human subject,
   (iv) detecting onset of decompensated heart failure in the remotely-located human subject based on the blended first and second output, and
   (v) generating a detection signal upon detecting onset of decompensated heart failure in the remotely-located human subject; and
   an electronic alert system operatively connected to the computing instance, the electronic alert system configured to automatically generate an electronic alert in response to the computing instance generating the detection signal, the electronic alert suggesting that the remotely-located human subject exhibits signs of onset of decompensated heart failure.

2. The detecting and alerting system of claim 1 wherein the second machine learning model is trained on the remotely-located human subject.

3. The detecting and alerting system of claim 1 wherein the blending comprises majority voting, plurality voting, or computing a weighted averaging of results from the first machine learning model and the second machine learning model.

4. The detecting and alerting system of claim 1 wherein the data receiver receives digitized voice samples from telecommunication devices including smartphones of the human subjects.

5. A detecting and alerting method for detecting onset of decompensated heart failure in remotely-located human subjects and automatically generating electronic intervention alerts based on detected onset, the detecting and alerting method comprising:
   receiving digitized voice samples of remotely-located human subjects;
   using a computing instance, performing operations comprising:
   (i) executing a first machine learning model trained on voice samples from a population to detect at least one feature in speech or voice characteristics that is a sign of onset of decompensated heart failure,
   (ii) executing a second machine learning model that analyzes changes in acoustic features of received voice samples from a remotely-located human subject over time,
   (iii) blending a first output from the first machine learning model based on voice samples received from the remotely-located human subject with a second output from the second machine learning model based on the received voice samples from the remotely-located human subject,
   (iv) detecting onset of decompensated heart failure in the remotely-located human subject based on the blended first and second output, and
   (v) generating a detection signal upon detecting onset of decompensated heart failure in the remotely-located human subject; and
   automatically generating an electronic alert in response to the computing instance generating the detection signal, the electronic alert suggesting that the remotely-located human subject exhibits signs of onset of decompensated heart failure.

6. The detecting and alerting method of claim 5 wherein the second machine learning model is trained on the remotely-located human subject.

7. The detecting and alerting method of claim 5 wherein blending includes computing a weighted average of results of the first machine learning model and the second machine learning model.

8. The detecting and alerting method of claim 5 wherein receiving includes receiving digitized voice samples produced by a smartphone.

9. The detecting and alerting method of claim 5 further including the computing instance storing labelled received digitized voice samples detected as indicative of onset of decompensated heart failure for application to the first machine learning model or the second machine learning model.

* * * * *